United States Patent [19]

Sahm et al.

[11] 4,087,610

[45] May 2, 1978

[54] PROCESS FOR THE PREPARATION OF 5-ACETOACETYLAMINO-BENZIMIDAZO-LONE

[75] Inventors: Wilfried Sahm, Kelkheim, Taunus; Ernst Hille, Rossert, Taunus; Wolfgang Schiller, Sulzbach, Taunus, all of Germany

[73] Assignee: Hoechst Aktiengesellschaft, Frankfurt am Main, Germany

[21] Appl. No.: 680,719

[22] Filed: Apr. 27, 1976

[30] Foreign Application Priority Data

Apr. 29, 1975 Germany .............................. 2518922

[51] Int. Cl.² .......................................... C07D 235/26
[52] U.S. Cl. .................................................. 548/305
[58] Field of Search ........................ 260/309.2, 562 K

[56] References Cited

U.S. PATENT DOCUMENTS

| 1,982,675 | 12/1934 | Law | 260/562 K |
| 2,152,132 | 3/1939 | Boese | 260/562 K |
| 3,963,694 | 6/1976 | Mory et al. | 260/309.2 |

FOREIGN PATENT DOCUMENTS

| 723,057 | 2/1955 | United Kingdom | 260/562 K |
| 770,263 | 3/1957 | United Kingdom | 260/562 K |
| 962,227 | 7/1964 | United Kingdom | 260/562 K |

*Primary Examiner*—Natalie Trousof
*Attorney, Agent, or Firm*—Curtis, Morris & Safford

[57] ABSTRACT

5-Acetoacetylamino benzimidazolone-(2) is obtained in high yield and excellent purity by reacting diketene with the aqueous solution of a salt of 5-amino-benzimidazolone-(2) and an acid having a pKa value of 1 to 7, preferably in the presence of an antioxidant and/or a reducing agent.

12 Claims, No Drawings

PROCESS FOR THE PREPARATION OF 5-ACETOACETYLAMINO-BENZIMIDAZOLONE

It is known from U.S. Pat. Nos. 1,982,675; 2,152,132 and 3,304,328 to prepare acetoacetylamides by reacting free amines with diketene. The reaction medium is either an inert organic solvent or water. When an organic solvent is used in which the starting substance is readily soluble, the diketenization occurs quickly and completely, but since the product is also readily soluble, it can be isolated only with difficulty. When the starting substance is only sparingly soluble, it is necessary to work in suspension to obtain reasonable space yields. But in this operation substantial amounts of starting material are inevitably occluded in the precipitating reaction product which leads to an end product of unsatisfactory purity making its direct use as coupling component for azo pigments impossible. The same is true when the operation is effected in aqueous suspension.

When the diketenization of 5-aminobenzimidazolone-(2) is effected by starting from an aqueous solution of the starting substance at an elevated temperature, to avoid the disadvantages mentioned above, the reaction product has a satisfactory quality, but the reaction volume is no longer tolerable because of the low solubility of said amine in water (about 1 part by weight of base in 30 parts of water).

Now, it was found that 5-acetoacetylaminobenzimidazolone-(2) is obtained economically and in excellent purity by reacting 5-aminobenzimidazolone-(2) in aqueous solution with diketene when the 5-aminobenzimidazolone-(2) is reacted in form of the salt of an acid having a pKa value from 1 to 7, preferably 3 to 7; especially 4 to 7. Especially preferred as starting substance is the salt of a low molecular alkanoic acid, especially a low molecular alkanoic acid of 1 to 4 carbon atoms, oxalic acid or phosphoric acid. For the polybasic acids the dissociation stage used for the formation of the salt is given by the pKa-ranges indicated. For phosphoric acid, the first and preferably the second dissociation stages are involved. In the case of phosphoric acid, it is especially advantageous to dissolve the 5-aminobenzimidazolone at first as the primary phosphate at about 80° to 100° C, to clarify the solution with a clarifying agent and to replace before the diketenization the second hydrogen atom of the phosphoric acid by an alkali metal atom, advantageously by adding one molar equivalent of sodium or potassium hydroxide, advantageously in the form of a 30 to 50 % by weight aqueous solution.

The reaction with the diketene is advantageously carried out at temperatures within the range of about 40° to 100° C, especially 60° to 100° C. Preferably, the diketene is added as quickly as possible ("in one shot"). The product is isolated advantageously between about 20° and 50° C.

As the salts used according to the invention are far more easily soluble than the free base, the process of the invention gives high space-time yields and an unobjectionable quality of the product.

To improve the quality of the product, it is advantageous to exclude the influence of the atmospheric oxygen, for example by superposing inert gas. But it is more advantageous to add an antioxidation agent which also binds the dissolved oxygen. Suitable antioxidants are alkali metal sulfites, hydrogen sulfites, disulfites or dithionites and sulfur dioxide. Preferred is sodium hydrogen sulfite.

Since the starting material is obtained technically by reducing the nitro compound, it is furthermore advantageous to add for technical qualities of the starting substance a reducing agent which reduces the 5-nitrobenzimidazolone, if still present, to the amino compound. This reduction is most simply effected by means of nascent hydrogen which is advantageously set free by adding zinc. The zinc ions so obtained are advantageously precipitated by adding phosphate ions and separated.

A combination of antioxidant and reducing agent is especially preferred.

The following Examples illustrate the invention. Percentages are by weight.

EXAMPLE 1

37.2 g of 5-aminobenzimidazolone-(2) were dissolved while stirring in a mixture of 530 ml of water and 8.5 ml of 85% phosphoric acid at about 90° C, stirred with 5 g of active charcoal for 60 minutes and subsequently clarified. 6.5 ml of 50% sodium hydroxide solution were added. At 80° C the total of 25 ml of diketene (96%) was introduced at once while stirring vigorously. The reaction mixture was cooled to 20° C, the 5-acetoacetylamino benzimidazolone-(2) was suction-filtered, washed with water and dried at 100° C in a circulating air drying cabinet.

Yield: 49.5 g of 5-acetoacetylamino benzimidazolone-(2) Decomposition point: 353° C.

EXAMPLE 2

The reaction was carried out as in Example 1 but instead of 50% sodium hydroxide solution 9.8 ml of 50% potassium hydroxide solution were added.

Yield: 49.3 g of 5-acetoacetylamino benzimidazolone-(2)

EXAMPLE 3

The reaction was carried out as in Example 1, but 17 ml of 85% phosphoric acid and 13 ml of 50% sodium hydroxide solution were used. Yield: 49.3 g of 5-acetoacetylamino benzimidazolone-(2).

EXAMPLE 4

The reaction was carried out as in Example 2, but 17 ml of 85% phosphoric acid and 19.6 of 50% potassium hydroxide were used. Yield: 49.2 g of 5-acetoacetylamino benzimidazolone-(2).

EXAMPLE 5

37.2 g of 5-aminobenzimidazolone-(2) were dissolved while stirring in a mixture of 530 ml of water and 15 g of acetic acid (100%) at about 90° C, stirred with 5 g of active charcoal and then clarified. Then, 25 ml of diketene (96%) were added to the solution at 60° to 90° C. Working up was effected as described in Example 1.

Yield: 49.0 g of 5-acetoacetylamino benzimidazolone-(2).

EXAMPLE 6

37.2 g of 5-aminobenzimidazolone-(2) were dissolved while stirring in a mixture of 530 ml of water and 15 g of acetic acid (100%) at about 90° C. The so-obtained solution was stirred with 5 g of active charcoal and 0.5 g of zinc dust for about 10 minutes. 0.5 ml of 85% phosphoric acid were added and the mixture was clarified.

Then, 25 ml of diketene (96%) were added at 80° C and working up was effected as described in Example 1.

Yield: 49.3 g of 5-acetoacetylamino benzimidazolone-(2).

EXAMPLE 7

The reaction was carried out as in Example 1, but 7.5 ml of 40% sodium bisulfite solution were added additionally.

Yield: 49.2 g of 5-acetoacetylamino benzimidazolone-(2).

EXAMPLE 8

The reaction was carried out as in Example 1, but 7.5 ml of a 40% sodium bisulfite solution and 0.5 g of zinc dust were added additionally.

Yield: 49.3 g of 5-acetoacetylamino benzimidazolone-(2).

EXAMPLE 9

The reaction was carried out as in Example 5, but 7.5 ml of 40% sodium bisulfite were added additionally.

Yield: 49.5 g of 5-acetoacetylamino benzimidazolone-(2).

EXAMPLE 10

The reaction was carried out as in Example 6, but 7.5 ml of 40% sodium bisulfite solution were additionally added.

Yield: 49.3 g of 5-acetoacetylamino benzimidazolone-(2).

EXAMPLE 11

The reaction was carried out as in Example 10, but 11.5 g of formic acid were added instead of acetic acid.

Yield: 49.2 g of 5-acetoacetylamino benzimidazolone-(2).

EXAMPLE 12

The reaction was carried out as in Example 10, but 18.5 g of propionic acid were used instead of acetic acid.

Yield: 49.0 g of 5-acetoacetylamino benzimidazolone-(2).

EXAMPLE 13

The reaction was carried out as in Example 10, but 28 g of oxalic acid (monosodium salt) were used instead of acetic acid.

Yield: 49.2 g of 5-acetoacetylamino benzimidazolone-(2).

What is claimed is:

1. A process for the preparation of 5-acetoacetylamino benzimidazolone-(2) which comprises reacting diketene with an aqueous solution of a salt of 5-amino-benzimidazolone-(2) and an acid having a pKa value of 1 to 7, said solution containing an antioxidant and/or a reducing agent.

2. A process as claimed in claim 1, wherein the pKa range is 3 to 7.

3. A process as claimed in claim 1, wherein the pKa range is 4 to 7.

4. A process as claimed in claim 1, wherein the acid is an alkanoic acid of 1 to 4 carbon atoms, oxalic acid or phosphoric acid.

5. A process as claimed in claim 1, wherein the reaction temperature is 40° to 100° C.

6. A process as claimed in claim 1, wherein the reaction temperature is 60° to 100° C.

7. A process as claimed in claim 1, wherein the reaction is performed under exclusion of oxygen.

8. A process as claimed in claim 7, wherein the reaction is performed under inert gas cover.

9. A process as claimed in claim 1, wherein the antioxidant is an alkali metal sulfite, hydrogen sulfite, disulfites or dithionite or sulfur dioxide.

10. A process as claimed in claim 1, wherein the reducing agent is hydrogen in statu nascendi.

11. A process as claimed in claim 10, wherein zinc is added to the reaction solution and wherein the resulting zinc ions are separated from the reaction medium by precipitation with phosphate ions.

12. A process as claimed in claim 1, wherein the diketene is added to said aqueous solution as rapidly as possible.

* * * * *